United States Patent
Martin et al.

(10) Patent No.: US 7,977,103 B2
(45) Date of Patent: Jul. 12, 2011

(54) METHOD FOR DETECTING THE ONSET OF OVULATION

(75) Inventors: Stephanie Michelle Martin, Woodstock, GA (US); RameshBabu Boga, Alpharetta, GA (US); John Gavin MacDonald, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1455 days.

(21) Appl. No.: 11/408,154

(22) Filed: Apr. 20, 2006

(65) Prior Publication Data

US 2007/0249958 A1    Oct. 25, 2007

(51) Int. Cl.
G01N 33/48    (2006.01)
G01N 21/78    (2006.01)
A61B 10/00    (2006.01)

(52) U.S. Cl. ........... 436/65; 436/63; 436/119; 436/120; 436/164; 436/167; 436/169; 436/181; 422/400; 422/420; 422/83; 422/84; 422/85; 422/86; 422/87; 422/88; 73/23.3; 600/551

(58) Field of Classification Search ............... 436/63, 436/65, 119, 120, 139, 141, 164, 166, 167, 436/169, 174, 181; 422/55, 56, 61, 82.05, 422/83, 84, 85, 86, 87, 88, 400, 420, 430; 73/23.2, 23, 3; 600/551
See application file for complete search history.

(56) References Cited

U.S. PATENT DOCUMENTS

| | | | |
|---|---|---|---|
| 3,507,269 A | 4/1970 | Berry | |
| 3,836,633 A | 9/1974 | Beschke et al. | |
| 3,875,013 A * | 4/1975 | Manautou et al. | 435/18 |
| 4,119,089 A | 10/1978 | Preti et al. | |
| 4,385,125 A * | 5/1983 | Preti et al. | 436/65 |
| 4,407,960 A | 10/1983 | Tratnyek | |
| 4,469,746 A | 9/1984 | Weisman et al. | |
| 4,488,969 A | 12/1984 | Hou | |
| 4,780,448 A | 10/1988 | Broecker et al. | |
| 4,781,858 A | 11/1988 | Mizukami et al. | |
| 4,823,803 A | 4/1989 | Nakamura | |
| 4,854,332 A | 8/1989 | Hanakura | |
| 4,931,403 A * | 6/1990 | Cutler et al. | 436/65 |
| 5,100,581 A | 3/1992 | Watanabe et al. | |
| 5,122,418 A | 6/1992 | Nakane et al. | |
| 5,196,177 A | 3/1993 | Watanabe et al. | |

(Continued)

FOREIGN PATENT DOCUMENTS

| | | | |
|---|---|---|---|
| WO | WO 9606352 A1 | | 2/1996 |
| WO | WO 9705482 | | 2/1997 |
| WO | 2005/040794 | * | 5/2005 |
| WO | 2006/032719 | * | 3/2006 |

OTHER PUBLICATIONS

Freeman et al. Analyst, vol. 126, 2001, pp. 538-541.*

(Continued)

*Primary Examiner* — Maureen M Wallenhorst
(74) *Attorney, Agent, or Firm* — Dority & Manning, P.A.

(57) ABSTRACT

A method for detecting the onset of ovulation in a female mammal is provided. The method includes contacting mouth air of the female mammal with an arylmethane test chromogen in an amount effective to undergo a rapid and detectable color change in the presence of one or more volatile sulfur compounds. The color of the test chromogen is compared to a control color that corresponds to a pre-ovulatory sulfur content. The difference in color between the test chromogen and the control color is correlated to the onset of ovulation.

28 Claims, 1 Drawing Sheet

U.S. PATENT DOCUMENTS

| | | |
|---|---|---|
| 5,209,998 A | 5/1993 | Kavassalis et al. |
| 5,220,000 A | 6/1993 | Theodoropulos |
| 5,221,497 A | 6/1993 | Watanabe et al. |
| 5,230,953 A | 7/1993 | Tsugeno et al. |
| 5,266,289 A | 11/1993 | Tsugeno et al. |
| 5,332,432 A | 7/1994 | Okubi et al. |
| 5,338,713 A | 8/1994 | Takagi et al. |
| 5,342,876 A | 8/1994 | Abe et al. |
| 5,397,667 A | 3/1995 | Law et al. |
| 5,407,442 A | 4/1995 | Karapasha |
| 5,407,600 A | 4/1995 | Ando et al. |
| 5,420,090 A | 5/1995 | Spencer et al. |
| 5,429,628 A | 7/1995 | Trinh et al. |
| 5,458,864 A | 10/1995 | Tsugeno et al. |
| 5,467,778 A | 11/1995 | Catt et al. |
| 5,480,636 A | 1/1996 | Maruo et al. |
| 5,486,356 A | 1/1996 | Yim |
| 5,487,938 A | 1/1996 | Spencer et al. |
| 5,538,548 A | 7/1996 | Yamazaki |
| 5,580,655 A | 12/1996 | El-Shall et al. |
| 5,583,219 A | 12/1996 | Subramanian et al. |
| 5,591,797 A | 1/1997 | Barthel et al. |
| 5,597,512 A | 1/1997 | Watanabe et al. |
| 5,657,762 A | 8/1997 | Coley et al. |
| 5,721,142 A * | 2/1998 | Klemm et al. ............... 436/65 |
| 5,733,272 A | 3/1998 | Brunner et al. |
| 5,773,227 A | 6/1998 | Kuhn et al. |
| 5,817,300 A | 10/1998 | Cook et al. |
| 5,843,509 A | 12/1998 | Calvo Salve et al. |
| 5,880,176 A | 3/1999 | Kamoto et al. |
| 5,882,638 A | 3/1999 | Dodd et al. |
| 5,902,226 A | 5/1999 | Tasaki et al. |
| 5,914,271 A * | 6/1999 | Law et al. ............... 436/65 |
| 5,948,398 A | 9/1999 | Hanamoto et al. |
| 5,962,566 A | 10/1999 | Grandfils et al. |
| 5,985,229 A | 11/1999 | Yamada et al. |
| 5,989,510 A | 11/1999 | Abe et al. |
| 5,989,515 A | 11/1999 | Watanabe et al. |
| 6,004,625 A | 12/1999 | Ohshima |
| 6,024,786 A | 2/2000 | Gore |
| 6,039,923 A * | 3/2000 | Klemm et al. ............... 422/61 |
| 6,057,162 A | 5/2000 | Rounbehler et al. |
| 6,096,299 A | 8/2000 | Guarracino et al. |
| 6,123,676 A | 9/2000 | Anapliotis |
| 6,172,173 B1 | 1/2001 | Spencer et al. |
| 6,190,814 B1 | 2/2001 | Law et al. |
| 6,225,524 B1 | 5/2001 | Guarracino et al. |
| 6,234,974 B1 | 5/2001 | Catt et al. |
| 6,264,615 B1 | 7/2001 | Diamond et al. |
| 6,291,535 B1 | 9/2001 | Watanabe et al. |
| 6,299,867 B1 | 10/2001 | Aoyagi et al. |
| 6,334,988 B1 | 1/2002 | Gallis et al. |
| 6,344,272 B1 | 2/2002 | Oldenburg et al. |
| 6,369,290 B1 | 4/2002 | Glaug et al. |
| 6,376,741 B1 | 4/2002 | Guarracino et al. |
| 6,403,380 B1 | 6/2002 | Catt et al. |
| 6,428,814 B1 | 8/2002 | Bosch et al. |
| 6,433,243 B1 | 8/2002 | Woltman et al. |
| 6,440,187 B1 | 8/2002 | Kasai et al. |
| 6,451,619 B1 | 9/2002 | Catt et al. |
| 6,454,726 B1 | 9/2002 | Catt et al. |
| 6,468,500 B1 | 10/2002 | Sakaguchi et al. |
| 6,548,264 B1 | 4/2003 | Tan et al. |
| 6,585,663 B1 | 7/2003 | Coley et al. |
| 6,589,562 B1 | 7/2003 | Shefer et al. |
| 6,607,711 B2 | 8/2003 | Pedersen |
| 6,623,848 B2 | 9/2003 | Brehm et al. |
| 6,638,918 B2 | 10/2003 | Davison et al. |
| 6,927,064 B1 | 8/2005 | Catt et al. |
| 7,582,485 B2 * | 9/2009 | Boga et al. ............... 436/113 |
| 2001/0023338 A1 | 9/2001 | Guarracino et al. |
| 2001/0031248 A1 | 10/2001 | Hall-Puzio et al. |
| 2001/0056246 A1 | 12/2001 | Rodriguez-Fernandez et al. |
| 2002/0110686 A1 | 8/2002 | Dugan |
| 2002/0111561 A1 | 8/2002 | Kaga |
| 2002/0128336 A1 | 9/2002 | Kolb et al. |
| 2002/0142937 A1 | 10/2002 | Carter et al. |
| 2002/0177621 A1 | 11/2002 | Hanada et al. |
| 2003/0013369 A1 | 1/2003 | Soane et al. |
| 2003/0100842 A1 | 5/2003 | Rosenberg et al. |
| 2003/0147956 A1 | 8/2003 | Shefer et al. |
| 2003/0181540 A1 | 9/2003 | Quellet et al. |
| 2003/0203009 A1 | 10/2003 | MacDonald |
| 2003/0203495 A1 * | 10/2003 | Rupp ............... 436/74 |
| 2004/0120904 A1 | 6/2004 | Lye et al. |
| 2004/0120921 A1 | 6/2004 | Quincy, III et al. |
| 2004/0142041 A1 | 7/2004 | MacDonald et al. |
| 2004/0235183 A1 | 11/2004 | Coley et al. |
| 2005/0084412 A1 | 4/2005 | MacDonald et al. |
| 2005/0084438 A1 | 4/2005 | Do et al. |
| 2005/0084464 A1 | 4/2005 | McGrath et al. |
| 2005/0084474 A1 | 4/2005 | Wu et al. |
| 2005/0084632 A1 | 4/2005 | Urlaub et al. |
| 2005/0084977 A1 | 4/2005 | Boga et al. |
| 2005/0085144 A1 | 4/2005 | MacDonald et al. |
| 2005/0085739 A1 | 4/2005 | MacDonald et al. |
| 2005/0112085 A1 | 5/2005 | MacDonald et al. |
| 2005/0130311 A1 | 6/2005 | Coley et al. |
| 2005/0171454 A1 | 8/2005 | Catt et al. |
| 2005/0196812 A1 | 9/2005 | Williams |
| 2008/0243015 A1 * | 10/2008 | MacDonald et al. ......... 600/530 |

OTHER PUBLICATIONS

Quincy, III et al., U.S. Appl. No. 10/723,761, filed Nov. 26, 2004, Odor Control in Personal Care Products.

MacDonald, et al., U.S. Appl. No. 10/955,316, filed Sep. 30, 2004, Odor-Reducing Quinone Compounds.

Fish, et al., U.S. Appl. No. 10/687,425, filed Oct. 16, 2003, Odor Absorbing Extrudables.

MacDonald, U.S. Appl. No. 10/137,052, filed Apr. 30, 2002, Metal Ion Modified high surface Area Materials for Odor Removal and Control.

MacDonald, et al., U.S. Appl. No. 10/687,270, filed Oct. 16, 2003, Visual Indicating Device for Bad Breath.

Abidogun, K.A., Ojengbcde, O.A., Fatukasi, U.I., (1993), "Prediction and detection of ovulation: An evaluation of the cervical mucus score." *African Journal of Medicine and Medical Science*, 22, 65-69.

Albrecht, B.H., Fernando, R.S., Regas, J., Betz, G., (1985), "A new method for predicting and confirming ovulation." *Fertility and Sterility*, 44(2), 200-5.

Antuni, J.D., Kharitonov, S.A., Hughes, D., Hodson, M.E., Barnes, P.J., (2000), "Increase in exhaled carbon dioxide during exacerbations of cystic fibrosis" *Thorax*, 55, 138-142.

Ashby, C.D., Danzer, H.C., Swerdloff, R.S., (1980), "Estrogen radioimmunoassay suitable for the monitoring of ovulation induction" *Clinical Chemistry*, 26, 1143-1146.

Article—*Standard Practice for Obtaining Spectrometric Data for Object-Color Evaluation*, Published by *ASTM International*, Designation: E 1164-02.

Behre, H.M., Kuhlage, J., Gabner, C., Sonntag, B., Schem, C., Schneider, H.P.G., Nicschlag, E., (2000), "Prediction of ovulation by urinary hormone measurements with the home use ClearPlan® Fertility Monitor: comparison with transvaginal ultrasound scans and serum hormone measurements." *Human Reproduction*, 15(12), 2478-2482.

Bischoff, R., Moenke-Wedler, T., Bischoff, G., (2000), "On-line detection of volatile compounds in human breath", *4th European Congress of Oto-Rhino Laryngology, head and neck surgery*, pp. 1369-1375.

Brunauer et al. Adsorption of Gases in Multimolecular Layers, Authors, *The Journal of the American Chemical Society*, vol. LX, Feb. pp. 309-319 (1938).

Collins, W.P., (1982), "Ovulation prediction and detection." *IPPF Medical Bulletin*.

Diskin, A.M., Spanel, P., Smith, D., (2003), "Increase of acetone and ammonia in urine headspace and breath during ovulation quantified using selected ion tube mass spectrometry" *Physiological Measurement*, 24, 191-199.

Djahanbakhch, O., Swanton, I.A., Corrie, J.E., McNeilly, A.S., (1981), "Prediction of ovulation by progesterone." *Lancet*, 2, 1164-1165.

Felton, M.J., (2004), "Sniffing Sinusitis" *Today's Chemist At Work*, Jun. 2004 (http://www.tcawonline.org).

Gnoth, C., Frank-Herrmann, P., Schmoll, A., Godehardt, E., Freundl, G., (2002), "Cycle characteristics after discontinuation of oral contraceptives." *Gynecology and Endocrinology*, 16(4), 307-17.

Horvath, I., Loukides, S., Wodehouse, T., et al, (1998), "Increased levels of exhaled carbon monoxide in bronchiectasis, a new marker of oxidative stress", *Thorax*, 53, 867-870.

Hunter, S. J., *Photoelectric Color Difference Meter. Opt Soc of America*, 48, pp. 985-995 (1958).

Ito, S., Kohli, Y., Kato, T., Abe, Y., Ueda, T. (1994), "Significance of ammonia produced by *helicobacter pylori*" *European Journal of Gastroenterology & Hepatology*, 6,167-174.

Kerin, J., (1982), "Ovulation Detection in the Human." *Clinical Reproduction and Fertility*, 1, 27-54.

Lamprecht, V.M., Grummer-Strawn, L., (1996), "Development of New Formulas to Identify the Fertile Time of the Mestrual Cycle." *Contraception*, 54, 339-343.

Lemoyne, M., Van Gossum, A., Kurian, R., Ostro, M., Axler, J., Jeejeebhoy, K.N., (1987), "Breath pentane analysis as an index of lipid peroxidation, a functional test of vitamin E status" *American Journal of Clinical Nutrition*, 46, 267-272.

Li, H., Chen, J., Overstreet, J.W., Nakajima, S.T., Lasley, B.L., (2002), "Urinary follicle-stimulating hormone peak as a biomarker for estimating the day of ovulation." *Fertility and Sterility*, 77(5), 961-966.

Loweit, K., Hoppichler, F., Ledermüller, G., (1990), "Ovulation prediction from cyclic changes in salivary electrical conductivity." *American Journal of Obstetrics and Gynecology*, 163(2), 708-710.

McArdle, C.R., Seibel, M., Weinstein, F., Hann, L.E., Nickerson, C., Taymor, M.L., (1983), "Induction of ovulation monitored by ultrasound" *Radiology*, 148, 809-812.

Megraud, F. et al., (2005), "Comparison of non-invasive tests to detect *helicobacter pylori* infection in children and adolescents, results of a multicenter European study" *Journal of Pediatrics*, 146, 198-203.

Moreno, J.E., Khan-Dawood, F.S., Goldzieher, J.W., (1997), "Natural Family Planning: Suitability of the CUE™ Method for Defining the Time of Ovulation." *Contraception*, 55, 233-237.

Philips, M., Greenburg, J., (1992), "Ion-trap detection of volatile organic compounds in alveolar breath" *Clinical Chemistry*, 38, 60-65.

Prout, R.E., et al, (1970) A Relationship Between Human Oral Bacteria and the Menstrual Cycle,., *The Journal of Periodontology*, pp. 30-33.

Rea, J., Williams, D., (2002), "Shaping exhale durations for breath CO detection for men with mild mental retardation" *Journal of Applied Behavior Analysis*, 35, 415-418.

Queiroz, C.S., Hayacibara, M.F., Tabchoury, C.P., Marcondes, F.K., Cury, J.A., (2002), "Relationship between stressful situations, salivary flow rate and oral volatile sulfur-containing compounds" *European Journal of Oral Sciences*, 110, 337-340.

Sehnert, S.S., Jiang, L., Burdick, J.F., Risby, T.H., (2002), "Breath biomarkers for detection of human liver diseases, preliminary study" *Biomarkers*, 7, 174-187.

Skelley, D.S., (2000), "E-nose technologies promise new diagnostic instruments" *IVD Technology*, January-February issue.

Springfield, J.R., Levitt, M.D., (1994), "Pitfalls in the use of breath pentane measurements to assess lipid peroxidation" *Journal of Lipid Research*, 35, 1497-1504.

Tonzetich, J., Preti, G., Huggins, G.R., (1978A), "Changes in Concentration of Volatile Sulfur Compounds of Mouth Air during the Menstrual Cycle" *Journal of International Medical Research*, 6, 245-254.

Tonzetich, J., (1978B), "Oral malodour: an indicator of health status and oral cleanliness" *International Dental Journal*, 28, 309-19.

Velasco-Garcia, M.N., Mottram, T., (2001), "Biosensors in the livestock industry: an automated ovulation prediction system for dairy cows." *TRENDS in Biotechnology*, 19(11), 433-434.

de Winder-de Groot, K.M., van der Ent, C.K., Prins, I., Tersmette, J.M., Uiterwaal, C.S.P.M., (2005), "Exhaled nitric oxide, the missing link between asthma and obesity" *Journal of Allergy and Clinical Immunology*, 115, 419-420.

Yamaya, M., Sekizawa, K., Ishizuka, S., et al, (1998), "Increased carbon monoxide in exhaled air of subjects with upper respiratory tract infections", *Journal of Respiratory Critical Care Medicine*, 158, 311-314.

Zayasu, K., Sekizawa, K., Okinaga, S. et al, (1997), "Increased carbon monoxide in exhaled air of asthmatic patients", *Journal of Respiratory Critical Care Medicine*, 156, 1140-1143.

Web Article, Nissl, Jan,—WebMd Medical Reference from Healthwise—(Apr. 20, 2006), Infertility & Reproduction Health Center, http://my.webmd.com/hw/infertility_reproduction/hw214032.asp.

Product Data Sheet, Ovulation Test Kits, http://www.babyhopes.com.

Web Article—"*Progesterone and it's role in getting pregnant*" http://www.babyhopes.com/articles/progesterone.html.

Web Article—Clearview Easy LH—Rapid Diagnostic for Ovulation, (May 1, 2007) http://www.clearview.com/casylhabout.cfm.

Product Data Sheet, Clearblue Easy, drugstore.com, inc. (1999-2007) http://www.drugstore.com.

Product Data Sheet, Breathe E-Z Systems, Inc., (2004) http://www.testbreath.com.

Product Data Sheet, MaybeMOM, http://www.maybemom.com/how_works.html.

Product Data Sheet, WOOMB, World Organisation Ovulation Method Billings, Ovulation Method Research and Reference Center of Australia (2002) http://www.woomb.org/centres.html.

Product Data Sheet, OvaCue, (1999-2007),Zertek, Inc. http://www.zetek.net.

Web Article, "*Compare fertility monitors for practicality and value*", (1999-2007),Zertek, Inc http://www.zetek.net/compare_fertility_monitors.htm.

Web Article, "*Ovulation prediction basics*", (1999-2007), Zertek, Inc http://www.zetek.net/ovulation_prediction.htm.

Béné, A. et al., "Applicability of a SPME Method for the Rapid Determination of VOCs"*Chima*, 56, No. 6, ISSN 0009-4293, pp. 289-291, 2002.

Santra, S. et al., "Development of novel dye-doped silica nanoparticles for biomarker application", *Journal of Biomedical Optics*, vol. 6, No. 2, Apr. 2001, pp. 160-166.

Abstract—*A sorbent tube for oral malodour monitoring*, Julia Rodríguez-Fernández, Regina López-Fernández, Rosario Pereiro, Manuel Menéndez, JoséMaria Tejerina, Alberto Sicilia, and Alfredo Sanz-Medel, Talanta, vol. 62, 2004, pp. 421-426.

Abstract—*Optical fibre sensor for hydrogen sulphide monitoring in mouth air*, Julio Rodríguez-Fernández, Rosario Pereiro, and Alfredo Sanz-Medel, Analytica Chimica Acta, vol. 471, 2002, pp. 13-23.

Article—*Significance of Ammonia in the Genesis of Gastric Epithelial Lesions Induced by Heliobacter Pylori: An in vitro Study with different bacterial and Urea Concentrations*, P Sommi, et al. Digestion, vol. 57, 1996, pp. 299-304.

Article—*Ammonia vapour in the mouth as a diagnostic marker for Helicobacter pylori infection: preliminary "proof of principle" pharmacological investigations*, C.D.R. Dunn, et al., British Journal of Biomedical Science, vol. 58, 2001, pp. 66-76.

Article—*Validation of $^{13}C$-Urea Breath Test for the Diagnosis of Helicobacter Pylori Infection in the Singapore Population*, T.S. Chua, et al., Singapore Medical Journal, vol. 43, No. 8, 2002, pp. 408-411.

Article—*Spectrophotometric Assay of Thiols*, Peter C. Jocelyn, Methods in Enzymology, vol. 142, 1987, pp. 44-67.

Search Report and Written Opinion for PCT/IB2007/050974, Oct. 26, 2007.

The Journal of International Medical Research; J. Tonzetich, G. Preti and G.R. Huggins; vol. 6, No. 3, 1978; "Changes in Concentration of Volatile Sulphur Compounds of Mouth Air During the Menstrual Cycle"; pp. 245-254.

International Dental Journal; Joseph Tonzetich, PhD; vol. 28, No. 3, Sep. 1978; Oral Malodour: An Indicator of Health Status and Oral Cleanliness; pp. 309-319.

Journal of Chromatography, 226(1981); James G. Kostelc, George Preti, Philip R. Zelson, Joseph Tonzetich, George R. Huggins; Volatiles of Exogenous Origin From the Human Oral Cavity; pp. 315-323.

* cited by examiner

METHOD FOR DETECTING THE ONSET OF OVULATION

BACKGROUND OF THE INVENTION

The menstrual cycle is a complicated process involving many different hormones, women's sex organs and the brain. Two of the most important hormones of the pituitary gland are follicle stimulating hormone (FSH) and leuteinizing hormone (LH). The pituitary gland is a small gland at the base of the brain which controls all the activity of the sexual organs and their development. At the start of each menstrual cycle, the pituitary gland releases FSH, which causes the immature eggs (follicles) to grow. While the follicle is developing, the cells around the egg produce estrogen, which causes the lining of the uterus to grow each month to prepare it for receiving a fertilized egg. Once the follicle has reached a certain size and development milestone, the rising level of estrogen in the blood signals to the pituitary gland that the ovary is ready to release the egg. The pituitary gland then sends out a high level of LH, which likewise signals the ovary to release the egg for ovulation. This is commonly referred to as the "LH surge." The LH surge in human females occurs about 24 to 36 hours prior to the onset of ovulation and may last about 1 to 2 days (typically the 14th or 15th day of a normal 28-day menstrual cycle). During the LH surge, the concentration of LH is at least 3 times greater than the basal concentration. For instance, in human females, the LH surge level is between about 50 to 200 milli-International Units per milliliter ("mIU/ml) of urine, while the basal level is between about 6 to 13 mIU/ml.

Various tests have been developed that attempt to diagnose the onset of ovulation by detecting the LH surge. One such test kit is the "ClearBlue® Easy Ovulation Test Pack" (Unipath Diagnostics), which involves dipping a test stick into a cup of urine or in midstream urine. The kit consists of a membrane immobilized with antibodies to LH. As urine is wicked up the strip, the presence of LH will lead to the development of the test line. In each test, a control line must develop for the test to be valid. Though highly accurate, urinary LH-based detection devices are hardly convenient. They generally require the collection of a sample or capture of midstream urine for a specified time period. Then, the user must wait between 3 to 5 minutes to learn the results of the test. If a woman wants to test twice a day and works outside the home, this testing methodology may become very inconvenient. It may also be quite costly if women are using the test strips over the course of several months (especially twice a day) to predict the time of greatest fertility.

Due to the problems noted above, various techniques have been developed that attempt to monitor secondary indicators of ovulation. Several reports, for instance, have linked changes in the menstrual cycle with an increase in breath volatile sulfur in women. (*Tonzetich*, et al. (1978); *Queiroz*, et al. (2002)). More specifically, at the beginning of menstruation and during ovulation, the production of proteins in saliva increases, thereby providing bacteria with an increased food source. The number of bacteria in saliva may also experience an increase during both menstruation and ovulation. (*Prout*, et al., (1970)). Because bacteria produce volatile sulfur compounds through enzymatic action on proteins, it is believed that the increase in protein/bacteria levels leads to a corresponding increase in the generation of sulfurous compounds. Various sources have also indicated that a mid-cycle spike of oral volatile sulfur concentration exists in women. (*Tonzetich*, et al., (1978)). This increase in volatile sulfur compounds in the mid-cycle may thus provide an alternative method to predict ovulation.

Techniques have thus been developed to predict ovulation based on the presence of volatile sulfur compounds. For instance, U.S. Pat. No. 4,119,089 to Preti, et al., which is incorporated herein in its entirety by reference thereto for all purposes, describes a method that involves testing mouth air for volatile sulfur compounds. More specifically, Preti, et al. indicates that volatile sulfur content of mouth air "spikes" approximately 5 to 7 days prior to ovulation and again at the time of ovulation. Preti, et al. mentions several techniques for measuring sulfur content, including gas chromatography, 2,3,5-triphenyltetrazolium chloride ("TPTZ") colorimetric indicators, or trained animals (e.g., dogs) that can distinguish the volatile sulfur compounds.

Despite the benefits achieved, however, a need for improvement nevertheless remains. A need currently exists, for example, for a technique that more rapidly detects the onset of ovulation in a simple, non-invasive, and inexpensive manner.

SUMMARY OF THE INVENTION

In accordance with one embodiment of the present invention, a method for detecting the onset of ovulation in a female mammal is disclosed. The method comprises contacting mouth air of the female mammal with an arylmethane test chromogen in an amount effective to undergo a rapid and detectable color change in the presence of one or more volatile sulfur compounds. The color of the test chromogen is compared to a control color that corresponds to a pre-ovulatory volatile sulfur content. The difference in color between the test chromogen and the control color is correlated to the onset of ovulation. In one embodiment, for instance, the total absolute color difference ($\Delta E$) between the test chromogen and the control chromogen is at least about 3, the total absolute color change ($\Delta E$) being determinable by the following formula:

$$\Delta E = [(\Delta L^*)^2 + (\Delta a^*)^2 + (\Delta b^*)^2]^{1/2}$$

wherein, $\Delta L^*$ is the luminosity value of the control chromogen subtracted from the luminosity value of the test chromogen, each luminosity value ranging from about 0 to 100, where 0=dark and 100=light;

$\Delta a^*$ is the red/green axis value of the control chromogen subtracted from the red/green axis value of the test chromogen, each red/green axis value ranging from about −100 to 100, where positive values are reddish and negative values are greenish; and $\Delta b^*$ is the yellow/blue axis value of the control chromogen subtracted from the yellow/blue axis value of the test chromogen, each yellow/blue axis value ranging from about −100 to 100, where positive values are yellowish and negative values are bluish.

In accordance with another embodiment of the present invention, a test kit for detecting the onset of ovulation in a female mammal is disclosed. The test kit comprises a fibrous substrate containing an arylmethane test chromogen in an amount from about 0.001 wt. % to about 20 wt. % of the dry weight of the substrate. The test kit also comprises a vapor-impermeable material (e.g., film) that substantially encloses the fibrous substrate. The vapor-impermeable material defines an orifice that is configured to receive mouth air from the female mammal. Further, the test chromogen is configured to undergo a rapid and detectable color change in the presence of one or more volatile sulfur compounds, the color change indicating the onset of ovulation.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGURE in which.

Figure 1:
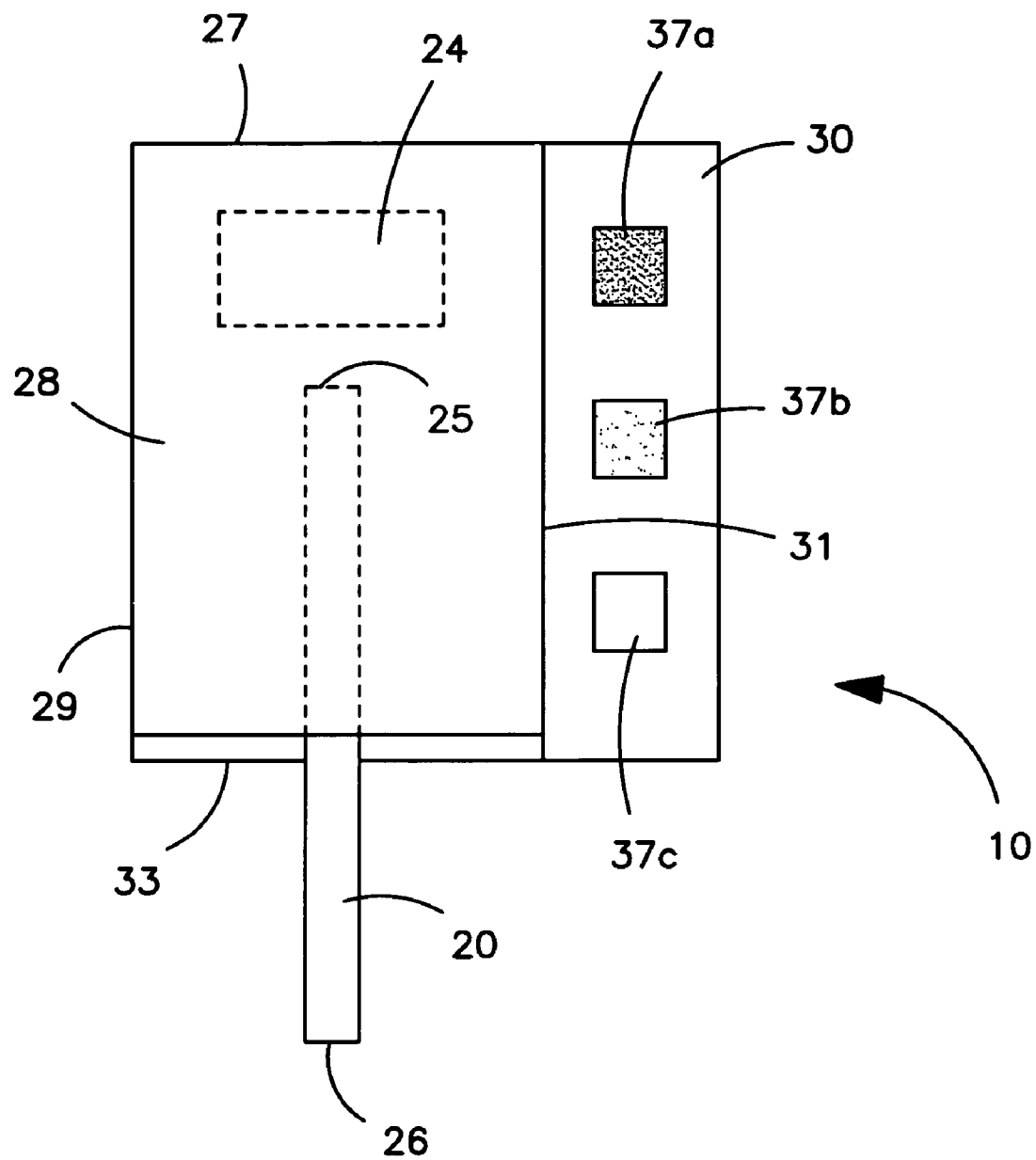
FIG. 1 illustrates one embodiment of a breath test kit that may be used in the present invention.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a simple and inexpensive breath test kit that may rapidly and non-invasively detect the onset of ovulation in a female mammal (e.g., human, cow, horse, etc.) to aid in conception or provide fertility awareness for contraception. More specifically, the breath test kit may be used to monitor mouth air for an increase in volatile sulfur content, which may likewise correspond to a spike in LH levels ("LH surge"). During an LH surge, for instance, the volatile sulfur content of mouth air may increase to a concentration that is at least about 1.5, in some cases at least about 2, and in some cases, from about 2 to about 5 times greater than a pre-ovulatory concentration. The increase in volatile sulfur content may occur about 24 to 36 hours prior to ovulation and may last about 1 to 2 days (typically the 14th or 15th day of a normal 28-day menstrual cycle). In this manner, the volatile sulfur content may be correlated to an LH surge, which in turn may be used as an indicator for the onset of ovulation.

To detect the increase in volatile sulfur content, the breath test kit contains a detection composition may be applied to a substrate. Various attributes of the composition and substrate are selectively controlled in accordance with the present invention to provide the breath test kit with excellent detection sensitivity in a short period of time. The detection composition, for instance, contains an arylmethane chromogen (e.g., triarylmethane, diarylmethane, etc.) that undergoes a rapid and detectable color change in the presence of volatile sulfur compounds. Volatile sulfur compounds that may be detected in accordance with the present invention include sulfates, sulfides, disulfides, sulfites, sulfonic acids, sulfuryls, thiocyanates, isothiocyanates, thioethers, thiols, thionyls, etc. Particular volatile sulfur compounds for detection in accordance with the present invention include hydrogen sulfide ($H_2S$), ethyl mercaptan ($CH_3CH_2SH$), methyl mercaptan ($CH_3SH$), and dimethyl sulfide (($CH_3)_2S$).

Without intending to be limited by theory, it is believed that sulfur groups of volatile sulfur compounds react with the central carbon atom of the arylmethane chromogen molecules. The reaction induces a shift of the absorption maxima towards the red end of the spectrum ("bathochromic shift") or towards the blue end of the spectrum ("hypsochromic shift"). The type of absorption shift depends on the nature of the chromogen molecule and on whether the sulfur group functions as an electron acceptor (oxidizing agent), in which a hypsochromic shift results, or whether the sulfur group functions as an electron donor (reducing agent), in which a bathochromic shift results. Regardless, the absorption shift provides a color difference that is detectable, either visually or through instrumentation, to indicate the presence of volatile sulfur compounds in mouth air. For example, prior to contacting mouth air, the chromogen may be colorless or it may possess a certain color. However, after contacting the breath and reacting with sulfur compounds present therein, the chromogen exhibits a change in color that is different than its initial color. That is, the chromogen may change from a first color to a second color, from no color to a color, or from a color to no color. As referred to herein, the term "color change" is intend to include a change from a color having a certain intensity to the same color, but at a different intensity (e.g., dark blue to light blue or light blue to dark blue).

Triarylmethane chromogens, for example, have the following general structure:

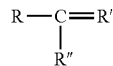

wherein R, R', and R" are independently selected from substituted and unsubstituted aryl groups, such as phenyl, naphthyl, anthracenyl, etc. The aryl groups may, for example, be substituted with functional groups, such as amino, hydroxyl, carbonyl, carboxyl, sulfonic, alkyl, and/or other known functional groups. An example of the structure of such a chromogen molecule after reaction with a sulfur functional group is set forth below:

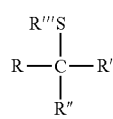

One example of a suitable triarylmethane chromogen is pararosaniline (also known as "basic fuchsin" or "magenta 0") and analogs thereof, such as rosanilin ("magenta I"), magenta II, new fuchsin ("magenta III"), methyl violet 2B, methyl violet 6B, methyl violet 10B ("crystal violet"), methyl green, ethyl green, acid fuchsin, and so forth. Pararosaniline shifts from a red color to colorless (i.e., white) upon reaction with a sulfur compound. Pararosaniline contains three phenylamine groups (i.e., amino-substituted aryl groups). Specifically, the structure of the structure of pararosaniline is set forth below:

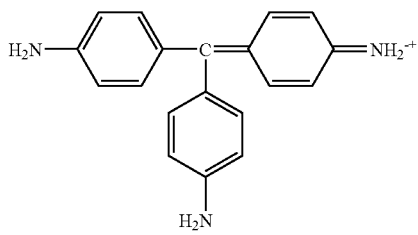

In some cases, triarylmethane chromogens may be formed by converting a leuco base to a colorless carbinol and then treating the carbinol with an acid to oxidize the carbinol and form the chromogen. Thus, for example, pararosaniline may be derived by reacting the carbinol form of pararosaniline ("pararosaniline base") with an acid, such as, but not limited to, sulfonic acids, phosphoric acids, hydrochloric acid, and so forth. The carbinol form of pararosaniline is set forth below.

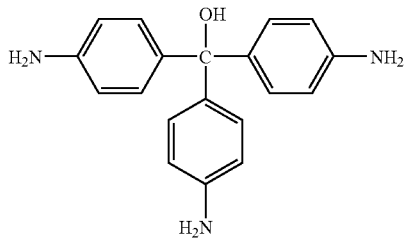

Another example of a suitable triarylmethane chromogen is alpha-naphtholbenzein and analogs thereof. Alpha-naphtholbenzein turns from an orange/red color to a gray/black color upon reaction with a sulfur compound. Alpha-naphtholbenzein contains a hydroxyl-substituted naphthyl group, a carbonyl-substituted naphthyl group, and a phenyl group. Specifically, the structure of alpha-naphtholbenzein is set forth below:

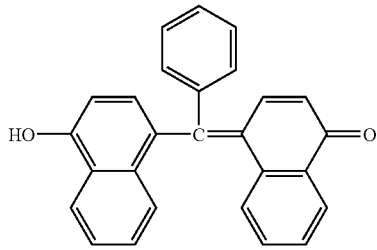

Still another example of a suitable triarylmethane chromogen is naphthocrome green and analogs thereof. Naphthocrome green turns from a pale yellow color to a blue/green color upon reaction with a sulfur compound. Similar to alpha-naphtholbenzein, naphthocrome green contains a hydroxyl-substituted naphthyl group, a carbonyl-substituted naphthyl group, and a phenyl group. However, each naphthyl group is also substituted with a sodium carboxyl. Specifically, the structure of naphthocrome green is set forth below:

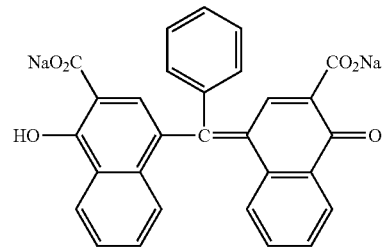

As indicated above, diarylmethanes may also be used in the present invention. One example of such a diarylmethane is 4,4'-bis(dimethylamino)benzhydrol (also known as "Michler's hydrol"), which has the following structure:

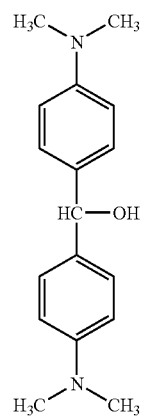

Michler's hydrol is a colorless carbinol. The carbinol form of Michler's hydrol may, however, be oxidized by an acid to form a blue chromogen. As indicated by the mechanism set forth below, the Michler's hydrol-based chromogen then changes from a blue color back to colorless upon reaction with a sulfur compound:

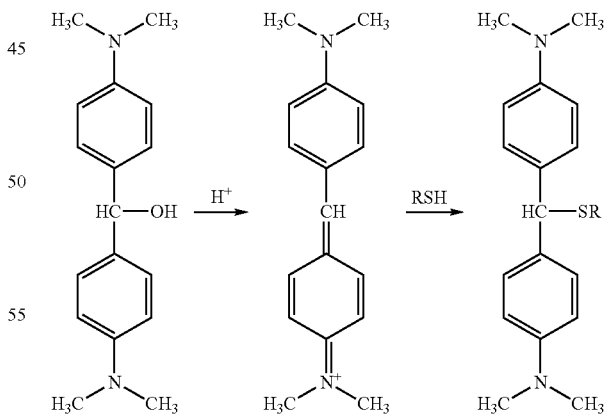

Still other examples of suitable arylmethane chromogens include analogs of Michler's hydrol, such as Michler's hydrol leucobenzotriazole, Michler's hydrol leucomorpholine, Michler's hydrol leucobenzenesulfonamide, and so forth.

Besides arylmethane chromogens, the detection composition may also contain other components. For example, the detection composition may contain a carrier for the chromogen that functions as a mobile phase. The carrier may be a liquid, gas, gel, etc., and may be selected to provide the desired performance (e.g., time for change of color, contrast between different areas, and sensitivity) of the chromogen. In some embodiments, for instance, the carrier may be an aqueous solvent, such as water, as well as a non-aqueous solvent, such as glycols (e.g., propylene glycol, butylene glycol, triethylene glycol, hexylene glycol, polyethylene glycols, ethoxydiglycol, and dipropyleneglycol); alcohols (e.g., methanol, ethanol, n-propanol, and isopropanol); triglycerides; ethyl acetate; acetone; triacetin; acetonitrile, tetrahydrafuran; xylenes; formaldehydes (e.g., dimethylformamide); etc. The amount of the carrier and chromogen in the detection composition may generally vary based on the level of sulfur sensitivity and color pattern or design utilized. For instance, in some embodiments, the chromogen may be present in the detection composition at a concentration from about 0.1 to about 100 milligrams per milliliter of carrier, in some embodiments from about 0.5 to about 60 milligrams per milliliter of carrier, and in some embodiments, from about 1 to about 40 milligrams per milliliter of carrier.

The detection composition may also contain additives for enhancing the performance of the arylmethane chromogen. For example, surfactants may help enhance the sensitivity of the chromogen and the contrast between different regions. Particularly desired surfactants are nonionic surfactants, such as ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, acetylenic diols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof. Commercially available nonionic surfactants may include the SURFYNOL® range of acetylenic diol surfactants available from Air Products and Chemicals of Allentown, Pa. and the TWEEN® range of polyoxyethylene surfactants available from Fischer Scientific of Pittsburgh, Pa.

The detection composition may also contain a binder to facilitate the immobilization of the arylmethane chromogen on a substrate. For example, water-soluble organic polymers may be employed as binders. One suitable class of water-soluble organic polymers includes polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

Although not required, the detection composition may be applied to a substrate for subsequent contact with mouth air. The substrate may be formed from any of a variety materials capable of being applied with the detection composition. For example, the substrate may be formed from a film, nonwoven web, knitted fabric, woven fabric, foam, etc. When utilized, the nonwoven webs may include, but are not limited to, spunbonded webs (apertured or non-apertured), meltblown webs, bonded carded webs, air-laid webs, coform webs, hydraulically entangled webs, and so forth. Examples of polymers that may be used to form such webs include, for instance, synthetic polymers (e.g., polyethylene, polypropylene, polyethylene terephthalate, nylon 6, nylon 66, etc.); cellulosic polymers (softwood pulp, hardwood pulp, thermomechanical pulp, etc.); combinations thereof; and so forth. In some embodiments, for example, the substrate is formed from pulp fibers, such as high-average fiber length pulp, low-average fiber length pulp, or mixtures of the same. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas-fir, true firs, pine (e.g., southern pines), spruce (e.g., black spruce), combinations thereof, and so forth. Northern softwood kraft pulp fibers may be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. Eucalyptus kraft pulp fibers may be particularly desired to increase softness, enhance brightness, increase opacity, and change the pore structure of the sheet to increase its wicking ability.

Any of a variety of known techniques may be used to apply the detection composition to the substrate, such as printing, dipping, spraying, melt extruding, coating (e.g., solvent coating, powder coating, brush coating, etc.), saturating, and so forth. The detection composition may be coated onto one or both surfaces of the substrate, or incorporated into the substrate matrix. In addition, the detection composition may cover an entire surface of the substrate, or may only cover a portion of the surface. For example, a substrate may be utilized that contains a detection zone that provides any number of distinct detection regions (e.g., lines, dots, etc.) so that a user may better determine the presence of volatile sulfur compounds. Each region may contain the same chromogen or different chromogens for reacting with different types of sulfur compounds. Upon application, the detection composition may be dried to remove the carrier and leave a residue of the chromogen for interacting with mouth air.

If desired, the substrate may also contain a control zone applied with a control chromogen that is the same or similar to the test chromogen. The control zone does not generally change color during testing so that it may be used for comparison. Similar to the detection zone, the control zone may also provide any number of distinct regions. For example, the control zone may contain regions corresponding to different predetermined sulfur concentrations, such as described above. In addition, the regions may contain chromogens that have a different sensitivity level for different types of sulfur compounds. Of course, the control zone need not be located on the same substrate as the test chromogen. In fact, in some embodiments, it may be desirable to employ a test strip containing the test chromogen and a separate control strip containing one or more control chromogens.

The amount of the chromogen applied to the substrate is effective to result in a detectable color change upon contact with a certain concentration of volatile sulfur compounds. The exact quantity may vary based on a variety of factors, including the sensitivity of the chromogen, the presence of other additives in the detection composition, the desired degree of detectability (e.g., with an unaided eye), etc. For example, a volatile sulfur concentration of from about 2 to about 8 nanograms per milliliter of mouth air may be indicative of an LH surge. Thus, the chromogen may be present in an amount sufficient to undergo a detectable color change in the presence of sulfur compounds at a concentration of at least about 2 nanograms per milliliter of mouth air. For example, the chromogen may constitute from about 0.001 wt. % to about 20 wt. %, in some embodiments from about 0.01 wt. % to about 10 wt. %, and in some embodiments from about 0.1 wt. % to about 5 wt. % of the dry weight of the substrate.

Although the chromogen of the present invention is capable of undergoing a detectable color change in the presence of very low sulfur concentrations, the color change is sometimes faint and not readily detectable by visual observation. The present inventors have discovered, however, that the results may be improved by enhancing the contact efficiency between the mouth air and chromogen. One technique used to accomplish such an enhanced contact efficiency involves increasing the effective surface area of the substrate. For example, particles may be applied to the substrate that have a high surface area, such as from about 50 square meters per gram ($m^2/g$) to about 1000 $m^2/g$, in some embodiments from about 100 $m^2/g$ to about 600 $m^2/g$, and in some embodiments, from about 180 $m^2/g$ to about 240 $m^2/g$. Surface area may be determined by the physical gas adsorption (B.E.T.) method of Bruanauer, Emmet, and Teller, Journal of American Chemical Society, Vol. 60, 1938, p. 309, with nitrogen as the adsorption gas. The particles may possess various forms, shapes, and sizes depending upon the desired result. For instance, the particles may be in the shape of a sphere, crystal, rod, disk, tube, string, etc. Likewise, the average size of the particles is generally less than about 500 microns, in some embodiments less than about 100 microns, in some embodiments less than about 100 nanometers, in some embodiments from about 1 to about 50 nanometers, in some embodiments from about 2 to about 50 nanometers, and in some embodiments, from about 4 to about 20 nanometers. As used herein, the average size of a particle refers to its average length, width, height, and/or diameter. If desired, the particles may be relatively nonporous or solid. That is, the particles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. It is believed that the solid nature, i.e., low pore volume, of the particles may enhance the uniformity and stability of the particles.

Any of a variety of particles may be used to provide the desired increase in effective surface area, so long as they do not adversely interfere with the ability of the chromogen to undergo a detectable color change in the presence of volatile sulfur compounds. For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), and so forth, may be used. Further, synthetic particles may also be utilized. For example, in one embodiment, latex particles may be employed, such as those formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Still other suitable particles include inorganic oxide particles, such as silica, alumina, zirconia, magnesium oxide, titanium dioxide, iron oxide, zinc oxide, copper oxide, zeolites, clays (e.g., smectite clay), combinations thereof, and so forth. Various examples of such inorganic oxide particles are described in U.S. Patent Application Publication Nos. 2003/0203009 to MacDonald; 2005/0084412 to MacDonald, et al.; 2005/0085144 to MacDonald, et al.; 2005/0084464 to McGrath, et al.; 2005/0084474 to Wu, et al.; and 2005/0084438 to Do, et al., which are incorporated herein in their entirety by reference thereto for all purposes.

Although not required, the "zeta potential" of the particles may be selected to optimize their functionality and/or ability to adhere to the substrate. For example, the particles may possess a negative zeta potential, such as less than about 0 millivolts (mV), in some embodiments less than about −10 mV, and in some embodiments, less than about −20 mV. Commercially available examples of particles having a negative zeta potential include Snowtex-C, Snowtex-O, Snowtex-PS, and Snowtex-OXS, which are silica nanoparticles available from Nissan Chemical of Houston, Tex. Alternatively, the particles may have a zeta potential of greater than about +20 millivolts (mV), in some embodiments greater than about +30 mV, and in some embodiments, greater than about +40 mV. By possessing a positive surface charge, the particles are well suited for being affixed to fibers that carry a negative surface charge (e.g., cellulosic fibers) through ionic attraction. Depending upon the difference in charge between the particles and the surface of the fibers (including van der Waals forces), the bond in some applications may be relatively permanent and substantive. Consequently, the particles may be affixed to fibers without the use of chemical binders or other attachment structures.

A positive zeta potential may be imparted to the particles of the present invention in a variety of different ways. In one embodiment, the particles are formed entirely from a positively charged material. For example, alumina particles may be used in with the present invention. Some suitable alumina particles are described in U.S. Pat. No. 5,407,600 to Ando, et al., which is incorporated herein in its entirety by reference thereto for all purposes. Further, examples of commercially available alumina particles include, for instance, Aluminasol 100, Aluminasol 200, and Aluminasol 520, which are available from Nissan Chemical Industries Ltd. Alternatively, the positive zeta potential may be imparted by a continuous or discontinuous coating present on the surface of a core material. In some instances, these particles may actually possess a better stability over various pH ranges than particles formed entirely from positively charged materials. In one particular embodiment, for example, the particles are formed from silica particles coated with alumina. A commercially available example of such alumina-coated silica particles is Snowtex-AK, which is available from Nissan Chemical of Houston, Tex.

The particles may be incorporated into the detection composition or applied separately (before or after). For example, the detection composition may be pre-coated onto the particles for subsequent application to the substrate. Alternatively, the particles may be applied to the substrate prior to application of the detection composition. In such embodiments, the particles may inhibit the diffusion of the detection composition through the matrix of the substrate. This enables a user to readily detect a change in color that occurs upon reaction of only a small amount of chromogen with a volatile sulfur compound. The particles may also be applied after application of the detection composition to improve the effective surface area over which the mouth air is able to contact the substrate.

The amount of particles applied to the substrate may generally vary depending on the nature of the particles, chromogen, and substrate. For instance, the particles may constitute from about 0.01 wt. % to about 30 wt. %, in some embodiments from about 0.1 wt. % to about 20 wt. %, and in some embodiments, from about 1 wt. % to about 15 wt. % of the substrate.

Another technique that may be used in the present invention to enhance the contact efficiency between the mouth air and chromogen involves restricting the loss of mouth air to the ambient environment. More specifically, the substrate may be substantially enclosed with a vapor-impermeable material that inhibits the passage of mouth air to the ambient environment and increases the likelihood that it will contact the chromogen. The vapor-impermeable material may be formed from a variety of materials as is well known in the art. For example, the vapor-impermeable material may be a film formed from a polyolefin polymer, such as linear, low-density polyethylene (LLDPE) or polypropylene. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers. Desirably, the vapor-impermeable material is substantially transparent or translucent so that the color change may be readily detected.

The vapor-impermeable material may be sealed so as to define an orifice through which a user may blow mouth air. The orifice may be covered before and/or after use. To assist the user, a mouthpiece may be positioned adjacent to the orifice. The mouthpiece may contain two open ends, one of which is adjacent to or near the substrate for delivering mouth air thereto and the other of which is exposed to the ambient environment for receiving the mouth air. In another embodiment, the substrate is positioned within the mouthpiece so that mouth air will flow through one end of the member, contact the substrate, and exit the other end of the member. In such embodiments, one end of the mouthpiece may be closed. The mouthpiece may possess any desired shape and/or size. For example, the mouthpiece may be a tube, straw, channel, etc. Various configurations of such a member are described in U.S. Patent Application Publication No. 2005/0085379 to MacDonald, et al., which is incorporated herein in its entirety by reference thereto for all purposes.

Referring to FIG. 1, for instance, one embodiment of a breath test kit 10 is shown. As shown, the test kit 10 includes a substrate 24 that is coated with a detection composition (not shown) and high-surface area particles (not shown). A first end 25 of a straw 20 is positioned adjacent to the substrate 24. The first end 25 of the straw 20 and the substrate 24 are enclosed within a vapor-impermeable material 28 that is sealed along three sides 27, 29, and 31. At least a portion of the remaining side 33 of the material 28 remains open so that the first end 25 of the straw 20 may be inserted therethrough.

A user may then breath through a second end 26 of the straw 20 to initiate the test. The test kit 10 also contains a separate control substrate 30 having different colored zones 37a, 37b, and 37c for comparison with the color of the reacted chromogen. Although not necessarily required, it may be desired to seal the entire test kit 10 within a package (not shown) that inhibits the chromogen from contacting sulfur compounds and prematurely activate the color change reaction.

After a subject has breathed onto the substrate in accordance with the present invention, the color of the arylmethane chromogen is detected. One beneficial aspect of the present invention is that the color change is rapid and may be detected within a relatively short period of time. For example, the chromogen may undergo a detectable color change in less than about 5 minutes, in some embodiments less than about 2 minutes, in some embodiments less than about 1 minute, in some embodiments less than about 30 seconds, and in some embodiments, less than about 15 seconds. In this manner, the breath test kit may provide a "real-time" indication of the presence or absence of volatile sulfur content.

The degree that the chromogen changes color may be determined either visually or using instrumentation to provide a semi-quantitative and/or quantitative correlation to a change in volatile sulfur content. For example, the color of the reacted chromogen is compared to the color of a control chromogen, which may be formed from a compound that is the same or similar to the test chromogen with respect to its responsiveness to volatile sulfur compounds. Multiple control chromogens may likewise be employed that correspond to different concentrations of sulfur compounds. For instance, five control chromogens may be utilized that are reacted with volatile sulfur compounds at various known concentrations. The concentration of the volatile sulfur compounds (or range of concentrations) within the mouth air is then determined from the selected control dye(s) and the corresponding known volatile sulfur content. Qualitative (i.e., yes or no), quantitative (i.e., a specific concentration), or semi-quantitative (i.e., a range of concentrations) results may thus be obtained using this technique.

If desired, the color intensity of the reacted chromogen may be measured to better determine volatile sulfur content. In one particular embodiment, an optical reader is used that measures color intensity as a function of absorbance. For example, absorbance readings may be measured using a conventional test known as "CIELAB", which is described in *Pocket Guide to Digital Printing* by F. Cost, Delmar Publishers, Albany, N.Y. ISBN 0-8273-7592-1 at pages 144 and 145 and "Photoelectric color difference meter", *Journal of Optical Society of America*, volume 48, page # 985-995, S. Hunter, (1958), both of which are incorporated herein in their entirety by reference thereto for all purposes. More specifically, the CIELAB method defines three "Hunter" scale values, $L^*$, $a^*$, and $b^*$, which correspond to three characteristics of a perceived color based on the opponent theory of color perception. The three values have the following meaning:

$L^*$=Lightness (or luminosity), ranging from 0 to 100, where 0=dark and 100=light;

$a^*$=Red/green axis, ranging approximately from −100 to 100; positive values are reddish and negative values are greenish; and $b^*$=Yellow/blue axis, ranging approximately from −100 to 100; positive values are yellowish and negative values are bluish.

Because CIELAB color space is somewhat visually uniform, a single number may be calculated that represents the total absolute color difference between two colors as perceived by a human using the following equation:

$$\Delta E = [(\Delta L^*)^2 + (\Delta a^*)^2 + (\Delta b^*)^2]^{1/2}$$

This difference is termed ΔE. In CIELAB color space, each ΔE unit is approximately equal to a "just noticeable" difference between two colors and is therefore a good measure for an objective device-independent color specification system that may be used as a reference color space for the purpose of color management and expression of changes in color. In accordance with the present invention, ΔE values of at least about 3, in some embodiments at least about 4, and in some embodiments, at least about 5, may be correlated to a spike in LH level, which is in turn may indicate the onset of ovulation.

The actual configuration and structure of an optical reader employed in the present invention may generally vary as is readily understood by those skilled in the art. Typically, the optical reader contains an illumination source that is capable of emitting electromagnetic radiation and a detector that is capable of registering a signal (e.g., transmitted or reflected light). The illumination source may be any device known in the art that is capable of providing electromagnetic radiation, such as light in the visible or near-visible range (e.g., infrared or ultraviolet light). For example, suitable illumination sources that may be used in the present invention include, but are not limited to, light emitting diodes (LED), flashlamps, cold-cathode fluorescent lamps, electroluminescent lamps, and so forth. The illumination may be multiplexed and/or collimated. In some cases, the illumination may be pulsed to reduce any background interference. Further, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source. One commercially available example of a suitable UV LED excitation diode suitable for use in the present invention is Model NSHU55OE (Nichia Corporation), which emits 750 to 1000 microwatts of optical power at a forward current of 10 milliamps (3.5-3.9 volts) into a beam with a full-width at half maximum of 10 degrees, a peak wavelength of 370-375 nanometers, and a spectral half-width of 12 nanometers.

In some cases, the illumination source may provide diffuse illumination to the chromogen. For example, an array of multiple point light sources (e.g., LEDs) may simply be employed to provide relatively diffuse illumination. Another particularly desired illumination source that is capable of providing diffuse illumination in a relatively inexpensive manner is an electroluminescent (EL) device. An EL device is generally a capacitor structure that utilizes a luminescent material (e.g., phosphor particles) sandwiched between electrodes, at least one of which is transparent to allow light to escape. Application of a voltage across the electrodes generates a changing electric field within the luminescent material that causes it to emit light.

The detector may generally be any device known in the art that is capable of sensing a signal. For instance, the detector may be an electronic imaging detector that is configured for spatial discrimination. Some examples of such electronic imaging sensors include high speed, linear charge-coupled devices (CCD), charge-injection devices (CID), complementary-metal-oxide-semiconductor (CMOS) devices, and so forth. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector may be a light sensor that lacks spatial discrimination capabilities. For instance, examples of such light sensors may include photomultiplier devices, photodiodes, such as avalanche photodiodes or silicon photodiodes, and so forth. Silicon photodiodes are sometimes advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into various types of detection systems. If silicon photodiodes are used, then the wavelength range of the emitted signal may be within their range of sensitivity, which is 400 to 1100 nanometers.

Correlation methods, such as described above, may be performed automatically and/or manually. For example, a microprocessor may optionally be employed to automatically convert the measurement from the detector to a result that quantitatively or semi-quantitatively indicates sulfur content. The microprocessor may include memory capability to allow the user to recall the last several results. Those skilled in the art will appreciate that any suitable computer-readable memory devices, such as RAM, ROM, EPROM, EEPROM, flash memory cards, digital video disks, Bernoulli cartridges, and so forth, may be used. If desired, the results may be conveyed to a user using a liquid crystal (LCD) or LED display.

The present invention may be better understood with reference to the following examples.

EXAMPLE 1

Materials Employed

A suspension of Snowtex-O particles (pH 4.1) was obtained from Nissan Chemical America of Houston, Tex. Unless otherwise indicated, all other chemicals were obtained from Sigma-Aldrich Chemical Co. of Milwaukee, Wis.

Breath Test Kit

A KIMWIPE® EX-L cellulosic sheet (Kimberly-Clark) was initially coated with the suspension of Snowtex-O particles (5 wt. %) and dried in air. Then, 10 microliters of a solution containing Michler's hydrol ("MH") chromogen in acetonitrile (1.5 milligrams per milliliter) was applied to the KIMWIPE® sheet. A blue color developed as the chromogen solution dried. A drinking straw was placed on an adhesive-backed plastic sheet. One end of the straw was placed on a small portion of white paper, which was then covered with a uniform MH-chromogen coated blue color. As a control, a small rectangular-shaped color strip was placed on a polyethylene cover and heat-sealed on all four sides. The test system was placed adjacent to the control and wrapped with a polyethylene cover and heat-sealed on all four sides. The resulting breath test kit was packaged in a foil structure (available from Banner Packaging, Inc.) and sealed with a silica gel desiccant pack (available from Royco) in the presence of nitrogen gas flushing.

Clinical Study Protocol

This protocol was performed according to the following procedures.

1. Subjects

Ten subjects who met the inclusion/exclusion criteria (detailed below) were recruited for this study. Subjects were recruited by an outside recruiting agency, according to the recruitment script approved by the study manager. The Investigator and/or study staff completed enrollment of consenting subjects and information for each individual was recorded on the study enrollment log.

Inclusion Criteria
  Signed informed consent form;
  Good general health;
  Women of childbearing potential between the ages of 18 and 42 years of age;
  Subjects that tested on study month 1 (for month 2); and
  Subject that are willing to meet the following rules prior to testing:
    Avoid sulfur producing foods 12 hours prior to testing, including:
      asparagus, cabbage, garlic, onions, broccoli, eggs, cheese, yogurt, milk and cauliflower
    Avoid consumption of all liquids (water in moderate amounts is acceptable)
    Avoid brushing of teeth and the use of mouth wash 2 hours prior to testing.

Exclusion Criteria
  History of, or exhibiting any signs or symptoms suggestive of systemic disease (i.e. chronic respiratory conditions or diabetes);
  Use of oral contraceptives or other contraceptive that prevents ovulation
  Known infertility condition;
  Use of medications or hormones to increase fertility;
  Known history of chronic halitosis; or
  Pregnancy or lactation.

Subjects could be terminated from further participation in the study for the following reasons:
  Non compliance with the protocol;
  Significant change in subject's general health; or
  Development of exclusion criteria during the study.

In the event of a subject's termination from the study, another subject who met the inclusion/exclusion criteria was to be recruited. The number of subject replacements in this study was to be based on the number of data sets required to complete the study (10 women).

Informed Consents—The purpose of the study and study requirements was completely explained to the subject. The subjects signed the informed consent form prior to the start of any study procedure. The study personnel offered each subject a signed copy of the consent form.

2. Experimental Design

Ten healthy female subjects were required for this study. The study lasted for approximately 2 months and took place at a Kimberly-Clark laboratory. Instructions for the subjects stated that, before coming to the laboratory, they must not have any food and must not brush their teeth. They were allowed to drink water, but other beverages were prohibited. The selected female subjects reported to the laboratory every morning (Monday through Friday) for the following tests. Each day, subjects provided a urine sample and blew into both a Halimeter® (available from Interscan Corporation) (3 readings) and into the breath test kit described above. The urine was used to determine if ovulation had occurred via a leuteinizing hormone (LH)-sensitive urine test kit. For each subject on each day, the result of the urine test (Y/N), the Halimeter® reading (in ppb), and the breath test kit result (Y/N for color change) were recorded. Additionally, a photograph of the breath test kit was taken daily using a digital camera.

This study required the following equipment:
  Halimeter®;
  250 breath test kits;
  250 urine-based ovulation prediction tests (ClearBlue® Easy Ovulation Test Pack available from Unipath Diagnostics); and
  Digital camera (for the daily recording of indicator results).

3. Randomization

The study was not randomized.

4. Schedule

It took each subject two menstrual cycles to complete the study. Additional make up times/days were scheduled if needed.

Procedure

Visits 1 through 10 were as follows
  1. Appointments were made for subjects to report to the laboratory every day (Monday through Friday) for two (2) consecutive weeks (repeated for two months) based on a typical cycle length as set forth below in Table 1:

TABLE 1

Day to Begin Testing for Typical Cycle Length

| Cycle Length | Cycle Day to Begin Testing |
|---|---|
| 21 | 5 |
| 22 | 6 |
| 23 | 7 |
| 23 | 8 |
| 25 | 9 |
| 26 | 10 |
| 27 | 11 |
| 28 | 12 |
| 29 | 13 |
| 30 | 14 |
| 31 | 15 |
| 32 | 16 |
| 33 | 17 |
| 34 | 18 |
| 35 | 19 |

Adjustments were made for cycle lengths outside of this range. Testing was completed between 11:30 am and 4:30 pm each day. The procedures performed each visit are set forth below in Table 2:

TABLE 2

Visit Schedule of the Subjects

| Visit No. | Day of Cycle for 26-32 day cycles | Activity |
|---|---|---|
| 1 | 11 ± 3 | Screen/enroll, Halimeter, Breath Test Kit, LH |
| 2 | 12 ± 3 | Halimeter, Breath Test Kit, LH |
| 3 | 13 ± 3 | Halimeter, Breath Test Kit, LH |
| 4 | 14 ± 3 | Halimeter, Breath Test Kit, LH |
| 5 | 15 ± 3 | Halimeter, Breath Test Kit, LH |

TABLE 2-continued

Visit Schedule of the Subjects

| Visit No. | Day of Cycle for 26-32 day cycles | Activity |
| --- | --- | --- |
| 6 | 18 ± 3 | Halimeter, Breath Test Kit, LH |
| 7 | 19 ± 3 | Halimeter, Breath Test Kit, LH |
| 8 | 20 ± 3 | Halimeter, Breath Test Kit, LH |
| 9 | 21 ± 3 | Halimeter, Breath Test Kit, LH |
| 10 | 22 ± 3 | Halimeter, Breath Test Kit, LH |

2. The nurse explained the study information and completed the consent process. After the subjects' questions had been answered and they had agreed to participate in the study, the following steps were completed:
   a. Medical and gynecologic history
   b. Inclusion/exclusion form
3. Subjects were questioned each time as to whether they had followed the dietary restrictions listed in inclusion criteria and if there had been any changes in their health status. Any deviations or abnormalities were documented.
4. The following steps were completed:
   a. A urine sample was provided by each subject to be tested for LH surge using the ovulation predictor kit (LH surge was indicated with a yes/no). The ovulation predictor kit was utilized according to package instructions.
   b. The subjects were instructed to breathe into the mouthpiece of the Halimeter® according to the manufacturer's instructions. The Halimeter® measures the volatile sulfur content from the breath. Three samples run in succession were suggested by the instructions and each subject reading was recorded in ppb. If the readings were above 200 ppb, or variability greater than 50 was observed, the test was repeated using a second Halimeter®.
   c. The study conductor then removed the desiccant package from the plastic wrap containing the breath test kit and instructed each subject to breathe two full breaths into the mouth piece (straw) of the breath test kit. A color change from blue to colorless was interpreted as indication of a positive result. No color change indicated a negative test.
   d. A digital photograph was taken of the breath test kit and control after removing the prototype from the plastic cover.
   e. The study conductor recorded the findings from steps a-d on a spreadsheet.
   f. The study conductor also documented the subject's detectable breath status (no odor, moderate odor, or strong odor) in the spreadsheet.
5. After the testing was completed each weekday, the subjects were instructed to continue dietary restrictions outlined in the list of foods to avoid and left the testing facility.

The same procedure (Steps 3-5) was repeated each day (Monday through Friday) for two consecutive weeks, and then repeated again for a second month.

6. Study Amendments and Deviations

Amendments were to be dated, justified and the impact on the study noted. The amendments were to be included in the study file. Any deviation to this protocol was to be dated, justified and the impact on the study noted by the Sponsor or Study Manager. Completed deviation reports are filed in the study file.

7. Data

All original data was entered into an Excel® spreadsheet and stored at Kimberly-Clark. A member of the technical staff sent an exported copy of the data to a Kimberly-Clark statistician for analysis.

8. Statistical Analysis

Comparison of the Halimeter® and LH surge test was conducted using four different approaches.

A first approach used a general linear statistical model to determine if a significant difference could be detected in Halimeter® readings when LH surge is detected versus when LH surge was not detected.

A second approach for comparing LH surge and Halimeter® responses was conducted by first averaging each respondent's Halimeter® values according to whether or not LH surge was detected. Therefore, for each individual cycle where LH surge was detected at least one time, two separate average Halimeter® responses were computed. These Halimeter® values were then compared using a statistical t-test to determine if the average Halimeter® response was higher when LH surge was detected.

A third approach for evaluating the relationship between the presence of LH surge and Halimeter® readings was conducted by comparing the Halimeter® reading for the first positive LH surge Halimeter® value to the preceding Halimeter® value. This analysis tests whether a jump in Halimeter® values is associated with the first occurrence of the detection of LH surge. Again, a pairwise t-test was utilized to evaluate the difference in successive Halimeter® readings upon the first occurrence of LH surge.

A fourth approach for evaluating the relationship between the presence of LH surge and Halimeter® readings was conducted by comparing the Halimeter® reading for the last positive LH surge Halimeter® value to the proceeding Halimeter® value. This analysis tests whether a drop in Halimeter® values is associated with the last occurrence of the detection of LH surge. Again, a pair wise t-test was utilized to evaluate the difference in successive Halimeter® readings upon the last occurrence of LH surge.

9. Results and Discussion

The first analysis conducted was to simply plot the data for each subject and observe any trends in the Halimeter® readings, especially near the time of ovulation. The results of the breath test kit were also analyzed and compared to the LH surge data with recorded breath test kit photos and to the Halimeter® data. A strong correlation did not appear to exist between the results of the breath test kit and the Halimeter®, or the results of the breath test kit and LH surge data. In an attempt to highlight general trends observed from the data after a preliminary analysis, a table was also created that addressed the following parameters: upward trend (assumed to be correlation) of Halimeter® with LH surge (yes/no), correlation of the breath test kit with LH surge (yes/no), and finally, whether or not there was an LH surge at all (yes/no). The results are set forth below in Table 3 (Month 1) and Table 4 (Month 2).

TABLE 3

Correlation of LH Surge with Increased Halimeter ® Reading or Positive Breath Test Kit Result (Month 1)

| | | | Correlation | |
| --- | --- | --- | --- | --- |
| Subject | Age | LH Surge (Yes or No) | LH Surge vs. Halimeter ® (yes or no) | LH Surge vs. Breath Test Kit (Yes or no) |
| 1 | 35 | Yes (day 14-17) | No | Yes |
| 2 | 29 | Yes (day 15-16) | Yes | Yes |
| 3 | 33 | Yes (day 14) | No | No |

TABLE 3-continued

Correlation of LH Surge with Increased Halimeter ® Reading or Positive Breath Test Kit Result (Month 1)

| Subject | Age | LH Surge (Yes or No) | Correlation LH Surge vs. Halimeter ® (yes or no) | LH Surge vs. Breath Test Kit (Yes or no) |
|---|---|---|---|---|
| 4 | 34 | Yes (day 10) | Yes | No |
| 5 | 32 | Yes (day 10) | Yes | No |
| 6 | 38 | Yes (day 12-13) | Yes | Yes |
| 7 | 39 | Yes (day 16) | Yes | Yes |
| 8 | 38 | No | — | — |
| 9 | 39 | No | — | — |
| 10 | 42 | No | — | — |

TABLE 4

Correlation of LH Surge with Increased Halimeter ® Reading or Positive Breath Test Kit Result (Month 2)

| Subject | Age | LH Surge (Yes or No) | Correlation LH Surge vs. Halimeter ® (yes or no) | LH Surge vs. Breath Test Kit (Yes or no) |
|---|---|---|---|---|
| 5 | 32 | Yes (day 11) | No | No |
| 2 | 29 | Yes (day 14-17) | Yes | Yes |
| 11* | 38 | Yes (day 10-11) | Yes | Yes |
| 10 | 42 | Yes (day 14) | No | No |
| 3 | 33 | Yes (day 14) | No | No |
| 8 | 38 | Yes (day 18-19) | Yes | No |
| 1 | 35 | Yes (day 14) | No | No |
| 6 | 38 | Yes (12) | Yes | No |
| 12* | 37 | Yes (12-13) | No | No |
| 9 | 39 | No | — | — |

*Subject Nos. 4 and 7 did not participate the second month. Thus, these subjects were added to the study to achieve a total of 10 subjects.

Using the first statistical approach described in the experimental methods section, it was determined that the average Halimeter® readings when LH surge was detected (67.47), was actually lower than when LH surge was not detected (68.17) (p-value <0.9008). This analysis thus was not statistically significant and did not offer a conclusive result concerning the correlation between LH surge and Halimeter® readings. Using the second statistical approach, the average Halimeter® value was also lower when the LH surge was detected (64.89) than when it was not (69.12). The non-significant p-value (p<0.6523) again failed to give a conclusive result about a correlation between the LH surge and the Halimeter®. Using the third statistical approach, the average preceding Halimeter® value (76.78) was slightly higher than the Halimeter® value associated with the first occurrence of LH surge (73.83). This analysis again resulted in a non-significant p-value (p<0.4404), providing an inconclusive result concerning the correlation between LH surge and Halimeter® readings. According to the fourth and final approach, the average proceeding Halimeter® value was slightly lower 67.20) than the Halimeter® value associated with the last occurrence of LH surge (77.80). The p-value of 0.2141 in this case was also not statistically significant, but was much lower than that of each of the previous analyses.

The dominant factor in the statistical analysis of the data appeared to be high degree of variability associated with the Halimeter® test. Another factor appeared to be that of sample size. A power analysis was performed based upon 80% power to detect a 15% change in Halimeter® values when LH surge is positive (alpha level 0.05). The estimated subject sample size was calculated to be 122 for a two tailed-test and 96 for a one-tailed test. The statistical data was largely impacted by the variability of the Halimeter® data. The sample size number calculated from the power analysis would most likely be reduced if there were less variability in the Halimeter® test. The analysis was further impacted by the inability to test on weekends, which resulted in many missing data points (sometimes near the time of ovulation). Although the statistical analysis did not show a significant correlation between the LH surge and increasing Halimeter® values, the data suggested a trend of increasing Halimeter® readings near the onset of ovulation.

EXAMPLE 2

Materials Employed

Snowtex-O (pH 4.1) particles were obtained from Nissan Chemical America of Houston, Tex. Unless otherwise indicated, all other chemicals were obtained from Sigma-Aldrich Chemical Co. of Milwaukee, Wis.

Breath Test Kit

A KIMWIPE®EX-L cellulosic sheet (Kimberly-Clark) was initially coated with a solution containing Snowtex-O particles (5 wt. %) and then dried in air. Then, 10 microliters of a solution containing Michler's hydrol ("MH") chromogen in acetonitrile (1.5 milligrams per milliliter) was applied onto the KIMWIPE® sheet. A blue color developed as the chromogen solution dried. The dye-coated sheet was then cut into 1.5 cm×2.0 cm strips and placed in a three-sided, heat-sealed Ziploc® plastic bag (available from S.C. Johnson & Son of Racine, Wis.). A drinking straw (5 to 6 centimeters in length) (available from Glad Products Company, Oakland, Calif.) was placed into the plastic bag containing the dye-coated strip. The straw was positioned just above the indicator strip. The fourth side of the bag was sealed with Scotch® transparent tape (available from 3M, St. Paul, Minn.). A color-coded control strip was heat sealed on the side of device to compare the color change of the indicator. The control strip was prepared by digital ink printing (McDermid-Colorspan wide format printer, Rockville, Md.) cyan ink squares (7 mm×7 mm) on a Ziplock® bag film. Four (4) squares in total were printed, side by side, each square having a Delta E value of 5 units less color that the previous square. In this manner, the printed strip had a series of blue squares (4 cm×7 cm) with decreasing blue hues so that the user could assess the degree of color change by comparison to the control grid. The icons were printed beside the control grid to convey the intensity of sulfur content to the user. The resulting breath test kit was packaged in a foil structure (available from Banner Packaging, Inc.) having an oxygen and moisture transmission rate of less than 0.01 grams per square meter per hour. The foil structure was sealed with a silica gel desiccant pack (available from Royco) in the presence of nitrogen gas flushing.

Clinical Study Protocol

A sufficient number of subjects who met the following inclusion/exclusion criteria described in Example 1 were recruited for this study to allow for completion of a minimum of 20 data sets. A data set consisted of each subject testing 12 breath test kits and 12 urine tests for LH. Subjects were recruited by an outside recruiting agency, according to the recruitment script approved by the study manager.

1. Experimental Design

Twenty healthy female subjects were required for this study. The study lasted for approximately two months and took place at a Kimberly-Clark laboratory. Instructions for subjects stated that, before coming to the laboratory, they must not have any food and must not brush their teeth. They were allowed to drink water, but other beverages were prohibited. The selected female subjects reported to the laboratory every morning (Monday through Friday) for the following tests. Each day, subjects provided a urine sample and blew into the breath test kit described above. The urine was used to determine if ovulation had occurred via a leuteinizing hormone (LH)-sensitive urine test kit. For each subject on each day, the result of the urine test (Y/N) and the breath test kit result (Y/N for color change) were recorded. Additionally, a photograph of the breath test kit was taken daily using a digital camera.

This study required the following equipment:
- 250 breath test kits;
- 250 urine-based ovulation prediction tests (ClearBlue® Easy Ovulation Test Pack available from Unipath Diagnostics);
- Digital camera (for the daily recording of indicator results); and
- Handheld spectrophotometer (from Minolta Co. Ltd., Osaka, Japan, Model # CR-300).

2. Procedure

Visits 1 through 10 were as follows
1. Appointments were made for subjects to report to the laboratory every day (Monday through Friday) for two (2) consecutive weeks (repeated for two months) based on a typical cycle length as set forth below in Table 5:

TABLE 5

Day to Begin Testing for Typical Cycle Length

| Cycle Length | Cycle Day to Begin Testing |
|---|---|
| 21 | 5 |
| 22 | 6 |
| 23 | 7 |
| 23 | 8 |
| 25 | 9 |
| 26 | 10 |
| 27 | 11 |
| 28 | 12 |
| 29 | 13 |
| 30 | 14 |
| 31 | 15 |
| 32 | 16 |
| 33 | 17 |
| 34 | 18 |
| 35 | 19 |

Adjustments were made for cycle lengths outside of this range. Testing was completed between 11:30 am and 4:30 pm each day. The procedures performed each visit are set forth below in Table 6:

TABLE 6

Visit Schedule of the Subjects

| Visit No. | Day of Cycle for 26-32 day cycles | Activity |
|---|---|---|
| 1 | 11 ± 3 | Screen/enroll, Breath Test Kit, LH |
| 2 | 12 ± 3 | Breath Test Kit, LH |
| 3 | 13 ± 3 | Breath Test Kit, LH |
| 4 | 14 ± 3 | Breath Test Kit, LH |
| 5 | 15 ± 3 | Breath Test Kit, LH |
| 6 | 18 ± 3 | Breath Test Kit, LH |
| 7 | 19 ± 3 | Breath Test Kit, LH |
| 8 | 20 ± 3 | Breath Test Kit, LH |
| 9 | 21 ± 3 | Breath Test Kit, LH |
| 10 | 22 ± 3 | Breath Test Kit, LH |

2. The nurse explained the study information and completed the consent process. After the subjects' questions had been answered and they had agreed to participate in the study, the following steps were completed:
   a. Medical and gynecologic history
   b. Inclusion/exclusion form
3. Subjects were questioned each time as to whether they had followed the dietary restrictions listed in inclusion criteria and if there had been any changes in their health status. Any deviations or abnormalities were documented.
4. The following steps were completed:
   a. Chromameter measurement of the breath test kit colored area was obtained in triplicate using the Minolta Chromameter CR-300™ (referred to hereinafter as "BSLN").
   b. A urine sample was provided by each subject to be tested for LH surge using the ovulation predictor kit (LH surge was indicated with a yes/no). The ovulation predictor kit was utilized according to package instructions.
   c. The study conductor then removed the desiccant package from the plastic wrap containing the breath test kit and instructed each subject to breathe two full breaths into the mouth piece (straw) of the breath test kit. After 2 to 5 minutes, the color was observed. A color change from blue to colorless was interpreted as indication of a positive result. No color change indicated a negative test. The color was compared to a standalone control strip for reference.
5. A test reading was taken of the breath test kit using the chromameter to evaluate the color change (referred to hereinafter as "TEST").
6. A digital photograph was taken of the visually positive breath test kit and control after removing the prototype from the plastic cover.
7. The study conductor recorded the findings from step 4 on a spreadsheet.
8. The study conductor documented the subject's breath status (no odor, moderate odor, or strong odor) in the spreadsheet.
9. After the testing had been completed, the subject was instructed to continue dietary restrictions outlined in the list of foods to avoid and was permitted to leave the testing facility.
10. The same procedure (Steps 4-9) was repeated each day (Monday through Friday) for two consecutive weeks.
11. On Friday of the first week, two specimen cups and two breath test kits, along with two plastic bags with desiccant were given to the subject to take home for the weekend. Subjects were instructed to collect and refrigerate a urine sample on Saturday and Sunday at approximately the same time each day. Subjects were also asked to blow into the breath test kit at this time, examine it briefly for a color change, and then return the breath test kit to the original package. The subjects then placed this package into the plastic bag with dessicant for future analysis. The urine samples were kept refrigerated until returning to the testing facility on Monday.

12. The study conductor took chromameter measurements for the breath test kits and tested the urine for LH surge.

3. Data

The data collected for this study are shown in Table 7.

TABLE 7

Summary of the Clinical Results

| Subject # | LH Surge (1 = Pos; 0 = Neg) | Cycle day | L*a*b* Values | | | Delta E |
|---|---|---|---|---|---|---|
| | | | L* | a* | b* | |
| 1 | 1 | 13 | BSLN 58.98 | 4.98 | −30.61 | 3.87 |
| | | | TEST 57.79 | 3.14 | −27.42 | |
| 2 | 0 | — | — | — | — | — |
| 3 | 1 | 14 | — | — | — | — |
| | 1 | 15 | BSLN 56.14 | 5.29 | −30.00 | 7.07 |
| | | | TEST 56.51 | 1.33 | −24.15 | |
| 4 | 1 | 9 | BSLN 56.64 | −1.13 | −19.85 | 14.08 |
| | | | TEST 68.10 | −0.8 | −11.67 | |
| | 1 | 12 | BSLN 59.73 | 4.95 | −28.98 | 6.99 |
| | | | TEST 58.74 | 0.48 | −23.69 | |
| | 1 | 14 | BSLN 56.49 | 3.41 | −25.26 | 1.72 |
| | | | TEST 57.21 | 1.95 | −25.83 | |
| | 1 | 16 | — | — | — | — |
| | 1 | 17 | — | — | — | — |
| | 1 | 18 | — | — | — | — |
| | 1 | 19 | — | — | — | — |
| | 1 | 20 | — | — | — | — |
| 5 | 1 | 14 | BSLN 57.83 | −0.70 | −21.25 | 2.41 |
| | | | TEST 59.69 | −1.36 | −19.87 | |
| | 1 | 15 | BSLN 53.64 | 2.37 | −26.30 | 10.23 |
| | | | TEST 60.94 | −1.77 | −20.44 | |
| 6 | 1 | 20 | BSLN 54.54 | 0.23 | −23.79 | 8.13 |
| | | | TEST 60.02 | −1.84 | −18.15 | |
| 7 | 1 | 19 | BSLN 57.99 | −0.90 | −22.40 | 3.47 |
| | | | TEST 58.82 | −1.98 | −19.21 | |
| 8 | 1 | 10 | BSLN 65.62 | 0.51 | −9.12 | 2.40 |
| | | | TEST 65.54 | 0.21 | −11.50 | |
| | 1 | 11 | BSLN 63.76 | −0.82 | −14.82 | 5.38 |
| | | | TEST 61.36 | −1.71 | −19.55 | |
| 9 | 1 | 15 | BSLN 59.16 | −1.59 | −20.36 | 6.92 |
| | | | TEST 62.41 | −3.03 | −14.42 | |
| 10 | 1 | 11 | BSLN 58.65 | −1.61 | −21.32 | 8.11 |
| | | | TEST 63.46 | −3.70 | −15.14 | |
| | 1 | 12 | BSLN 55.80 | −1.62 | −20.58 | 8.58 |
| | | | TEST 62.34 | −2.84 | −15.16 | |
| 11 | 1 | 12 | BSLN 60.51 | −2.04 | −20.46 | 4.43 |
| | | | TEST 61.74 | −2.45 | −16.22 | |
| | 1 | 13 | BSLN 57.21 | −2.64 | −16.92 | 1.45 |
| | | | TEST 57.51 | −2.70 | −15.50 | |
| 12 | 1 | 10 | BSLN 59.65 | 3.02 | −28.92 | 7.96 |
| | | | TEST 64.28 | −0.85 | −23.73 | |
| | 1 | 11 | BSLN 60.37 | −0.07 | −24.38 | 5.15 |
| | | | TEST 63.90 | −0.62 | −20.66 | |
| | 1 | 12 | BSLN 57.54 | −0.70 | −21.70 | 4.72 |
| | | | TEST 59.28 | −2.12 | −17.54 | |
| | 1 | 17 | BSLN 57.74 | −2.06 | −18.20 | 5.42 |
| | | | TEST 62.77 | −2.36 | −16.20 | |
| 13 | 1 | 13 | BSLN 59.40 | 0.15 | −24.07 | 2.44 |
| | | | TEST 60.61 | −1.05 | −22.33 | |
| | 1 | 14 | BSLN 52.78 | −0.69 | −19.69 | 8.64 |
| | | | TEST 59.31 | −0.69 | −16.75 | |
| 14 | 1 | 13 | BSLN 53.84 | 2.25 | −26.44 | 4.24 |
| | | | TEST 55.22 | 0.15 | −23.03 | |
| | 1 | 14 | BSLN 56.04 | 1.19 | −26.70 | 3.66 |
| | | | TEST 58.01 | −0.28 | −23.98 | |
| 15 | 1 | 16 | BSLN 63.11 | −2.69 | −17.21 | 5.91 |
| | | | TEST 66.70 | −2.82 | −12.52 | |
| | 1 | 17 | BSLN 58.67 | −0.69 | −25.42 | 2.73 |
| | | | TEST 56.80 | 0.35 | −23.72 | |
| 16 | 1 | 11 | BSLN 62.14 | −2.27 | −18.60 | 5.65 |
| | | | TEST 66.71 | −2.17 | −15.27 | |
| 17 | 1 | 14 | BSLN 60.73 | 0.08 | −26.26 | 8.95 |
| | | | TEST 68.07 | −1.35 | −21.33 | |
| | 1 | 15 | BSLN 57.70 | −2.10 | −17.61 | 4.05 |
| | | | TEST 61.60 | −2.55 | −16.58 | |
| | 1 | 16 | BSLN 59.71 | −1.62 | −20.62 | 6.36 |
| | | | TEST 64.78 | −3.47 | −17.25 | |

TABLE 7-continued

Summary of the Clinical Results

| Subject # | LH Surge (1 = Pos; 0 = Neg) | Cycle day | L*a*b* Values | | | |
|---|---|---|---|---|---|---|
| | | | L* | a* | b* | Delta E |
| 18 | 1 | 13 | BSLN 60.86 | −1.63 | −23.24 | 2.80 |
| | | | TEST 62.60 | −1.27 | −21.07 | |
| 19 | 1 | 12 | BSLN 61.86 | −2.47 | −20.39 | 2.54 |
| | | | TEST 63.26 | −0.75 | −21.62 | |
| 20 | 1 | 15 | BSLN 61.00 | −2.13 | −19.02 | 5.77 |
| | | | TEST 66.38 | −3.27 | −17.26 | |

A Delta E of 1.0 was achieved for each subject, which means that the color change as just perceptible to the human eye. Furthermore, 13 of the subjects (65%) had a Delta E>5 during ovulation, which would clearly be observable to the human eye. Table 8 provides a cross-tabulation of the visual breath test kit positive evaluations versus the Delta E ($\geqq$5) specifications.

TABLE 8

Visual Results vs. Delta E ($\geqq$5)

| | | Delta E ($\geqq$5) | | | |
|---|---|---|---|---|---|
| | | No | | Yes | Total |
| Visual BBI Positive | No | 92 | 64.8% | 50 35.2% | 142 |
| | Yes | 36 | 34.0% | 70 66.0% | 106 |

When a visual change in the indicator was detected, a Delta E$\geqq$5 measurement occurred 66% of the time. However, when a visual change was not detected, a Delta E ($\geqq$5) measurement still occurred 35.2% of the time. With a relative risk ratio of 1.88, the positive association of the visual change and Delta E measurements was significant at 95% confidence. Although a strong relationship existed between the visual change and the Delta E ($\geqq$5) indications, there were still 86 instances (34.7%) when the two did not agree. This could be caused by a number of factors. First, raising the cutoff value of 5 would produce fewer positive readings, while lowering it would generate significantly more. Also, a fair amount of human judgment was associated with the visual change evaluation. As previously indicated, a color graduation scale would assist a user when reading the test kit to help indicate intensity. Another reason for the occurrence of discrepancies between the visual observation and Delta E ($\geqq$5) indications could be due to the fact that the Delta E measurement accounted for color change in any direction, rather that a direction of blue to white.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for detecting the onset of ovulation in a female mammal, the method comprising:
   contacting mouth air of the female mammal with a substrate comprising nanoparticles and an arylmethane test chromogen wherein the arylmethane test chromogen is present in an amount effective to undergo a rapid and detectable color change in the presence of one or more volatile sulfur compounds;
   comparing the color of the test chromogen to a control color that corresponds to a pre-ovulatory volatile sulfur content; and
   correlating a difference in color between the test chromogen and the control color to the onset of ovulation.

2. The method of claim 1, wherein the volatile sulfur compounds include hydrogen sulfide, ethyl mercaptan, methyl mercaptan, dimethyl sulfide, or combinations thereof.

3. The method of claim 1, wherein the test chromogen is a diarylmethane.

4. The method of claim 3, wherein the test chromogen is 4,4'-bis (dimethylamino)benzhydrol or an analog thereof.

5. The method of claim 1, wherein the test chromogen is a triarylmethane.

6. The method of claim 5, wherein the test chromogen is pararosaniline, alpha-naphtholbenzein, naphthocrome green, or an analog thereof.

7. The method of claim 1, wherein the female mammal is a human female.

8. The method of claim 1, wherein, at the onset of ovulation, the volatile sulfur content in the mouth air is at least about 1.5 times greater than the pre-ovulatory volatile sulfur content.

9. The method of claim 1, wherein, at the onset of ovulation, the volatile sulfur content in the mouth air is at least about 2 times greater than the pre-ovulatory volatile sulfur content.

10. The method of claim 1, wherein, at the onset of ovulation, the volatile sulfur content is from about 2 to about 8 nanograms per milliliter of mouth air.

11. The method of claim 1, wherein the absence of color in the test chromogen indicates the onset of ovulation.

12. The method of claim 1, wherein the test chromogen constitutes from about 0.001 wt. % to about 20 wt. % of the dry weight of the substrate.

13. The method of claim 1, wherein the test chromogen constitutes from about 0.1 wt. % to about 5 wt. % of the dry weight of the substrate.

14. The method of claim 1, wherein the substrate is a fibrous web.

15. The method of claim 1, wherein the substrate contains cellulosic fibers.

16. The method of claim 1, wherein the substrate defines a detection zone containing the test chromogen and a control zone containing a control chromogen having the control color.

17. The method of claim 1, wherein a control chromogen is provided on a separate substrate, the control chromogen having the control color.

18. The method of claim 1, wherein the color change occurs in less than about 5 minutes.

19. The method of claim 1, wherein the color change occurs in less than about 1 minute.

20. The method of claim 1, wherein the difference in color is visually detected.

21. The method of claim 1, wherein the difference in color is measured.

22. The method of claim 1, wherein the total absolute color difference ($\Delta E$) between the color of the test chromogen and the control color is at least about 3, the total absolute color change ($\Delta E$) being determined by the following formula:

$$\Delta E = [(\Delta L^*)^2 + (\Delta a^*)^2 + (\Delta b^*)^2]^{1/2}$$

wherein, $\Delta L^*$ is the luminosity value of the control color subtracted from the luminosity value of the color of the test chromogen, each luminosity value ranging from about 0 to 100, where 0=dark and 100=light;

$\Delta a^*$ is the red/green axis value of the control color subtracted from the red/green axis value of the color of the test chromogen, each red/green axis value ranging from about −100 to 100, where positive values are reddish and negative values are greenish; and $\Delta b^*$ is the yellow/blue axis value of the control color subtracted from the yellow/blue axis value of the color of the test chromogen, each yellow/blue axis value ranging from about −100 to 100, where positive values are yellowish and negative values are bluish.

23. The method of claim 22, wherein the total absolute color difference ($\Delta E$) is at least about 4.

24. The method of claim 1, wherein the control color is provided by an arylmethane chromogen.

25. The method of claim 1, wherein the color of the test chromogen is compared to the color of a plurality of control chromogens, wherein the control chromogens each have a color corresponding to different known volatile sulfur contents.

26. The method of claim 1, wherein the nanoparticles have an average size of less than about 100 nanometers.

27. The method of claim 1, wherein the nanoparticles have a surface area of from about 50 to about 1000 square meters per gram.

28. The method of claim 1, wherein the nanoparticles include silica, alumina, or combinations thereof.

* * * * *